United States Patent [19]

Tanaka et al.

[11] Patent Number: 5,151,659
[45] Date of Patent: Sep. 29, 1992

[54] SURFACE POTENTIAL MEASURING SYSTEM

[75] Inventors: Kuniyoshi Tanaka, Yokohama; Shunji Shirouzu, Ayase; Minoru Ohta, Tokyo; Hideo Miyagawa, Yokohama, all of Japan

[73] Assignee: Kabushiki Kaisha Toshiba, Kawasaki, Japan

[21] Appl. No.: 515,419

[22] Filed: Apr. 27, 1990

[30] Foreign Application Priority Data

Apr. 28, 1989 [JP] Japan .................... 1-111616
Jun. 30, 1989 [JP] Japan .................... 1-166985

[51] Int. Cl.⁵ ............................ G01R 29/12
[52] U.S. Cl. ......................... 324/458; 324/457
[58] Field of Search ................... 324/458, 457

[56] References Cited

U.S. PATENT DOCUMENTS

| | | | |
|---|---|---|---|
| 3,443,224 | 5/1969 | Kramer et al. | 324/457 X |
| 3,729,675 | 4/1973 | Vosteen | 324/457 X |
| 4,134,137 | 1/1979 | Jacobs et al. | |
| 4,147,981 | 4/1979 | Williams | |
| 4,433,298 | 2/1984 | Palm | 324/457 |
| 4,797,620 | 1/1989 | Williams | 324/458 |
| 4,800,337 | 1/1989 | Cox et al. | 324/457 X |
| 4,878,017 | 10/1989 | Williams | 324/458 X |

FOREIGN PATENT DOCUMENTS

| | | |
|---|---|---|
| 0156217 | 3/1985 | European Pat. Off. |
| 6037568 | 8/1983 | Japan |
| 62-55129 | 11/1987 | Japan |
| 1542837 | 3/1979 | United Kingdom |

OTHER PUBLICATIONS

Journal of Physics, E: Scientific Instruments, vol. 17, No. 9, Sep. 1984 pp. 788-792.
Instruments & Experimental Techniques, vol. 27, No. 4, Jul./Aug. 1984 pp. 1016-1018, New York, N. T. Yunda, "Meter for the Distribution of Surface Potential".

*Primary Examiner*—Kenneth A. Wieder
*Assistant Examiner*—Maura K. Regan
*Attorney, Agent, or Firm*—Oblon, Spivak, McClelland, Maier & Neustadt

[57] ABSTRACT

In a system for measuring a surface potential of a sample, a probe is located above. A surface of the sample with a small gap and is vibrated by a piezoelectronic element which is energized by a oscillator. A potential of the distal end of the probe is changed and is converted into an electrical signal. The surface potential is obtained from the electrical signal.

56 Claims, 15 Drawing Sheets

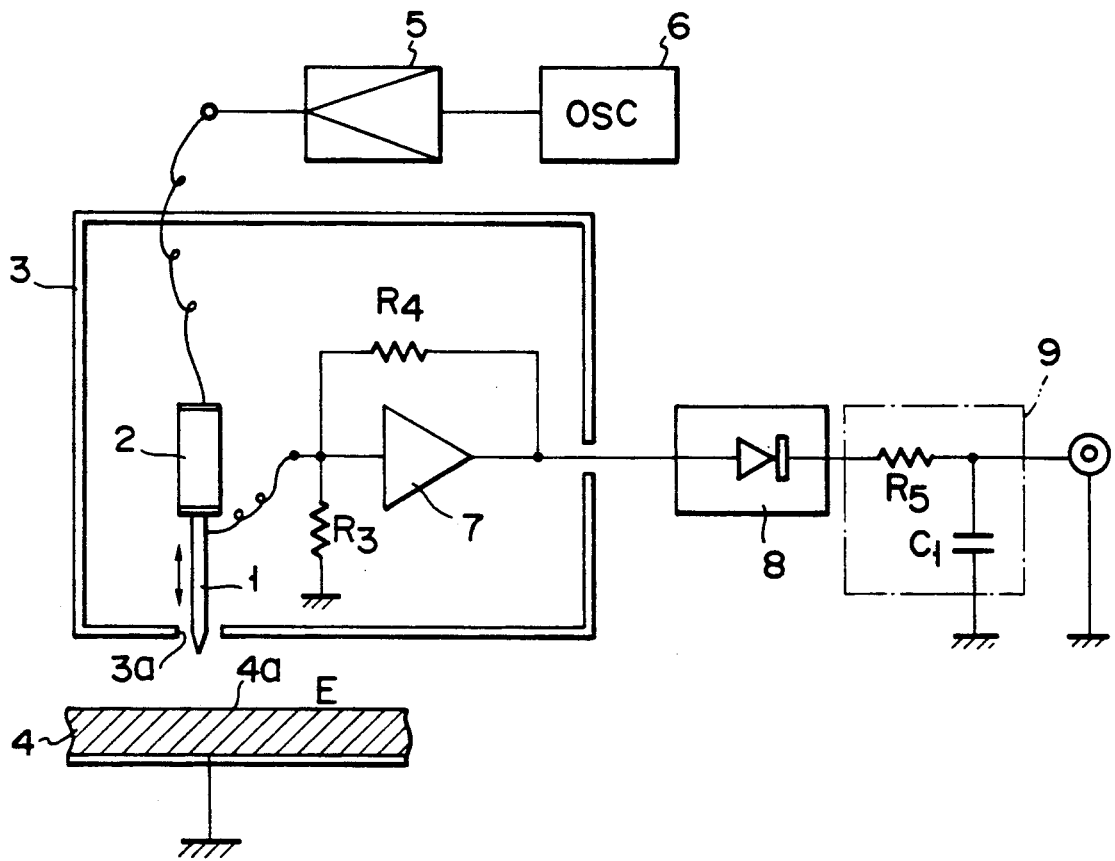
F I G. 2

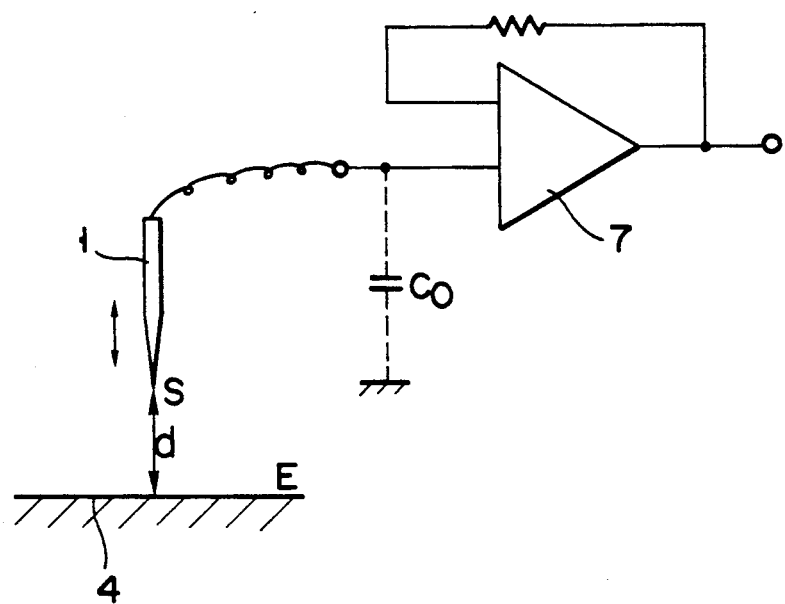
F I G. 3

SURFACE POTENTIAL MEASURING SYSTEM

BACKGROUND OF THE INVENTION

1. Field of the Invention

The present invention relates to a vibration type probe structure for measuring the surface potential of a surface of a sample in a noncontact manner and a surface potential measuring system using the same.

2. Description of the Related Art

As a conventional system for measuring charges on a surface of a sample, a noncontact type surface potential measuring system shown in FIG. 1 is known. In the system shown in FIG. 1, a measurement hole 100a is formed in the bottom of a shield case 100, and a flat sample 102 having a surface potential E is placed under the measurement hole 100a. A flat probe electrode 101 is arranged in the shield case 100 so as to oppose the sample 102 at a predetermined distance. A sector 103 as a shutter is arranged between the measurement hole 100a and the probe electrode 101. The sector 103 is connected to a solenoid 104 for driving the sector 103, a solenoid driver 105 for energizing the solenoid 104, and an oscillator 106 for generating an oscillation signal. A signal generated by the oscillator 106 is amplified by the solenoid driver 105 and is supplied to the solenoid 104. The solenoid 104 then drives the sector 103. The sector 103 is moved parallel to the measurement hole 100a to open and close it. In addition, an amplifier 107 and a synchronous detection circuit 108 are connected to the probe electrode 101 through resistors R1 and R2 and a capacitor C.

In this conventional surface potential measuring system, some of lines of electric force extending from the surface of the sample 102 reach a surface of the probe electrode 101 through the measurement hole 100a, and their amount $\phi$ is changed at a constant period upon an opening/closing operation of the sector 103. Therefore, a current proportional to $d\phi/dt$ flows through the load of the probe electrode 101, and an AC voltage e having a predetermined period is generated across the two ends of the capacitor R1 upon the opening/closing operation of the sector 103. The AC voltage e is proportional to the surface potential E of the sample 102 provided that the amplitude and frequency of the sector 103 and the distance from the probe electrode 101 to the sample 102 are constant.

The AC voltage e detected by the probe electrode 101 has a much smaller level than the surface potential E of the sample 102. For this reason, the AC voltage e is amplified by the amplifier 107 to a predetermined level and is converted into a DC voltage by the synchronous detection circuit 108 in synchronism with the oscillation frequency of the oscillator 106, i.e., the opening/closing operation of the sector 103 so as to be output as a measurement signal.

In this conventional surface potential measuring system, in order to obtain a measurement output proportional to the surface potential E of the sample 102, a signal to be detected by the probe electrode 101 must be a signal which is not much influenced by external noise and has a predetermined level or more.

For this purpose, the surface area of the probe electrode 101 must be increased, and the measurement hole 100a must be formed to have a predetermined size or more (generally, 3 mm square or more). In the conventional surface potential measuring system, therefore, the surface potential E of the sample 102 cannot be measured unless the sample 102 has an area of about 10 mm$^2$ or more. That is, a surface potential in a small area smaller than an area of 10 mm$^2$ cannot be measured. In addition, since the selector 103 as a shutter is arranged between the probe electrode 101 and the sample 102, the distance between the probe electrode 101 and the sample 102 is undesirably increased, resulting in poor detection sensitivity.

Furthermore, in the conventional noncontact type surface potential measuring system, a detection current value error is caused upon measurement due to temperature drift and the like. For example, the bias current of a detection amplifier is changed with a change in temperature, whereas the permittivity of a capacitance determined by the sample and the probe structure is changed with a change in humidity. Therefore, such an error must be corrected.

For this purpose, in the conventional system, prior to measurement, a reference voltage is applied to a conductive plate arranged in place of the sample 102. The reference voltage is changed, and a value measured by the surface potential measuring system at this time is calibrated. Thereafter, the sample 102 is placed under the system so as to measure its surface potential.

In such a method, however, a measurement value under the conditions of calibration is changed over time due to drift such as temperature drift. In order to perform high-precision measurement, therefore, measurement must be quickly started and completed after calibration so as to prevent the influences of temperature drift and the like. However, if, for example, a transfer drum used for a copying machine or a transfer disk used for a system for measuring the surface potential of a disk is a sample, since it has a large measurement area, a long measurement time is required. As a result, a measurement error caused by temperature drift and the like cannot be neglected, and stable, high-precision measurement cannot be performed.

SUMMARY OF THE INVENTION

It is an object of the present invention to provide a vibration type probe which has good detection sensitivity and can measure a surface potential within a small area with high precision, and a surface potential measuring system using the same.

It is another object of the present invention to provide a surface potential measurement sample from which a stable, high-precision measurement value can be obtained, and a system for correcting the measurement value.

According to the present invention, there is provided a system for measuring a surface potential of a sample, comprising:

probe means, having a distal end located near a measurement surface with a gap, for probing the surface potential;

vibrating means for vibrating the probe means to change the gap between the distal end and the measurement surface; and detecting means for detecting a change in potential of the distal end of the probe means and converting the change into a measurement signal corresponding to the surface potential of the sample.

In addition, according to the present invention, there is provided a system for measuring a surface potential of a sample having a surface region, comprising:

probe means, having a distal end located near a measurement surface with a gap, for probing the surface potential of the measurement surface;

vibrating means for vibrating the probe means to change the gap between a distal end of the probe means and the measurement surface;

holding means for holding the probe means, which is vibrated by the vibrating means, so as to allow the probe means to be vibrated;

means for maintaining a substantially constant gap between the holding means and a region retrieved by the probe means; and detecting means for detecting a change in potential of the vibrated distal end of the probe means and converting the change into a measurement signal corresponding to a surface potential of the sample.

In addition, according to the present invention, there is provided a sample whose surface potential is to be measured, comprising:

a surface whose surface potential is to be measured; and means, arranged on the surface, for receiving a reference potential.

Furthermore, according to the present invention, there is provided a system for reading a radiation image, comprising:

an image plate obtained by stacking a phosphor layer sensitive to radiation and emitting light and a photosensitive layer sensitive to the light emitted from the phosphor layer on a substrate, a latent image corresponding to a radiation transmission image being formed on the image plate;

means for urging a dielectric recording sheet against the photosensitive layer of the image plate so as to transfer the latent image formed on the photosensitive layer onto the dielectric recording sheet; and means for reading the latent image by measuring a potential of the latent image transferred onto the dielectric recording sheet and converting the potential into an electrical signal.

Moreover, according to the present invention, there is provided a system for reading a radiation image, comprising:

an image plate obtained by stacking a phosphor layer sensitive to radiation and emitting light and a photosensitive layer sensitive to the light emitted from the phosphor layer on a substrate;

a charger for uniformly charging the photosensitive layer of the image plate;

a dielectric recording sheet for transferring a latent image which is formed on the photosensitive layer in accordance with a radiation transmission image formed on the image plate;

a transfer roller for urging the dielectric recording sheet against the photosensitive layer of the image plate on which the latent image is formed; and means for reading the latent image by measuring a potential of the latent image transferred onto the dielectric recording sheet and converting the potential into an electrical signal.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a block diagram showing a system for measuring the surface potential of a sample, which incorporates a vibration type probe structure according to an embodiment of the present invention;

FIG. 3 is a view for explaining a principle of measurement by means of the vibration type probe structure in FIG. 2;

DETAILED DESCRIPTION OF THE PREFERRED EMBODIMENTS

Figure 1:
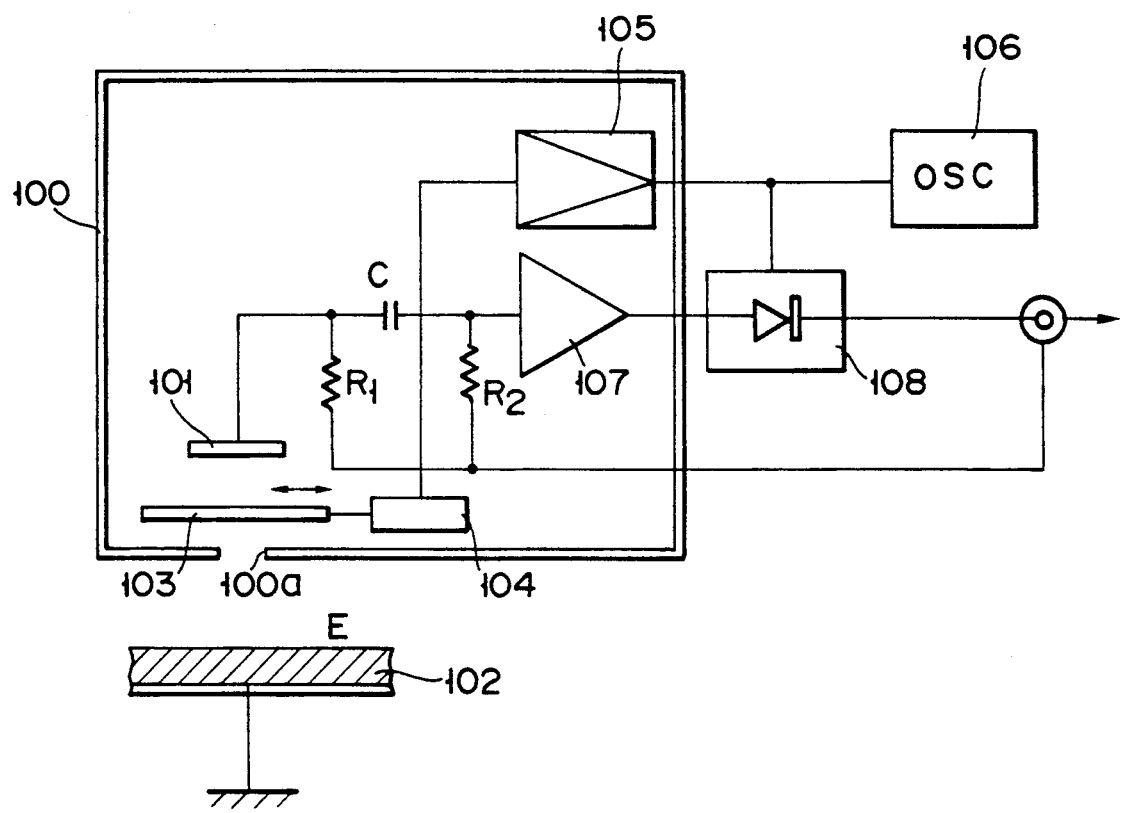
FIG. 1 is a block diagram showing a conventional system for measuring the potential of a surface of a sample to be measured.

FIG. 2 shows a vibration type probe structure according to the present invention and a system for measuring a surface potential distribution of a sample to be measured by using the same. As shown in FIG. 2, the vibration type probe structure is constituted by a needle-like probe electrode 1 and a piezoelectric element 2 coupled to the upper portion of the probe electrode 1. The probe electrode 1 is arranged in a shield case 3 having a measurement hole 3a formed in its bottom in such a manner that the distal end of the probe electrode 1 opposes a flat sample 4 having a surface potential E, which is located under the measurement hole 3a, at a predetermined distance. A piezoelectric driver 5 and an oscillator 6 are connected to the piezoelectric element 2 for vibrating the probe electrode 1 in a direction perpendicular to a measurement surface of the sample 4 as indicated by arrows in FIG. 2. A signal generated by the oscillator 6 is amplified by the piezoelectric element driver 5 and is supplied to the piezoelectric element 2. The piezoelectric element 2 is then driven. As a result, the probe electrode 1 is vertically vibrated. A synchronous detection circuit 8 and an integrator 9 consisting of a resistor R5 and a capacitor C1 are connected to the probe electrode 1 through resistors R3 and R4 and an amplifier 7. The position of the sample 4 is fixed. A measurement surface 4a (to be subjected to measurement) facing the probe electrode 1 is formed on the sample 4 so as to be flat with a sufficient surface precision.

In the surface potential measuring system including the vibration type probe structure according to the present invention, when the oscillator 6 is oscillated to generate an oscillation signal, and the oscillation signal is amplified by the piezoelectric element driver 5 so as to vertically vibrate the piezoelectric element 2, the probe electrode 1 coupled to the piezoelectric element 2 is also vertically vibrated at the oscillation frequency of the oscillator 6. When the probe electrode 1 is vertically vibrated at a predetermined period, since the distance from the measurement surface 4a of the sample 4 located under the probe electrode 1 to the probe electrode 1 is periodically changed, some of lines of electric force which are generated from the measurement surface 4a in accordance with the period reach the probe electrode 1. Therefore, as described above, a signal detected by the probe electrode 1 is generated as an AC signal which has the vibration period of the piezoelectric element 2 and is proportional to a surface potential E of the measurement surface 4a. The AC signal is amplified by the amplifier 7 and is subjected to synchronous detection in the synchronous detection circuit 8 at the same period as the vibration period of the probe electrode 1. The signal is then averaged by the integrator 9 and is output as a measurement value corresponding to the surface potential E of the measurement surface 4a.

A principle of measuring the surface potential of a sample by using the vibration type probe structure shown in FIG. 2 will be described with reference to FIG. 3. Assume, as shown in FIG. 3, that the surface area of the distal end of the probe electrode 1 is represented by S, the distance between a vibrating center which is defined as an intermediate point of a vibration range of the distal end of the probe electrode 1 and the sample 4 is represented by d, and a specific permittivity is represented by s. In this case, if only the distal end of the probe electrode 1 is influenced by lines of electric force from the sample 4, a capacitance C1 between the distal end of the prove electrode 1 and the sample 4 is represented by:

$$C_1 = \varepsilon \cdot s \cdot S / d \quad (1)$$

If the equivalent input capacitance of a detector system 7 constituted by an amplifier and the like which is connected to the probe electrode 1 is represented by C0, the surface potential E of the sample 4 is divided by capacitors C1 and C0. Therefore, a voltage across the two ends of the capacitor C0, i.e., a detection voltage Ed detected by the probe electrode 1 is represented by $$Ed = C1 \cdot E / (C1 + C0) \quad (2)$$

In this case, if the probe electrode 1 is vibrated by the vibrating element 2 such as a piezoelectric element at an arbitrary predetermined period in a direction perpendicular to the sample 4, since the distance d between the probe electrode 1 and the sample 4 is periodically changed, the value of C1 given by equation (1) is changed accordingly. With the change in C1, the detection voltage Ed detected by the probe electrode 1 is output as an AC signal obtained by modulating the surface potential E of the sample 4 with the vibrations of the probe electrode 1 according to equation (2).

According to equations (1) and (2), detection sensitivity for the detection voltage Ed detected by the probe electrode 1 can be improved by increasing the value of C1. For this purpose, the probe electrode 1 is located nearer to the sample 4 to decrease the distance d between the probe electrode 1 and the sample 4. In order to obtain a high-precision, stable measurement result, the distance d between a vibrating center of the probe electrode 1 and the sample 4 is preferably held in a constant.

With such a vibration type probe structure in which the distal end of the probe electrode 1 is located near and opposite the measurement surface 4a, stable, high-precision measurement of a surface potential can be performed with respect to the sample 4 whose position is fixed and which has the measurement surface 4a formed to be flat with sufficient surface precision.

Since the distal end of the probe electrode 1 is located near the measurement surface 4a, the detection sensitivity is improved, and the detection resolution can be increased. This allows high-precision measurement in a small area.

Figure 4:
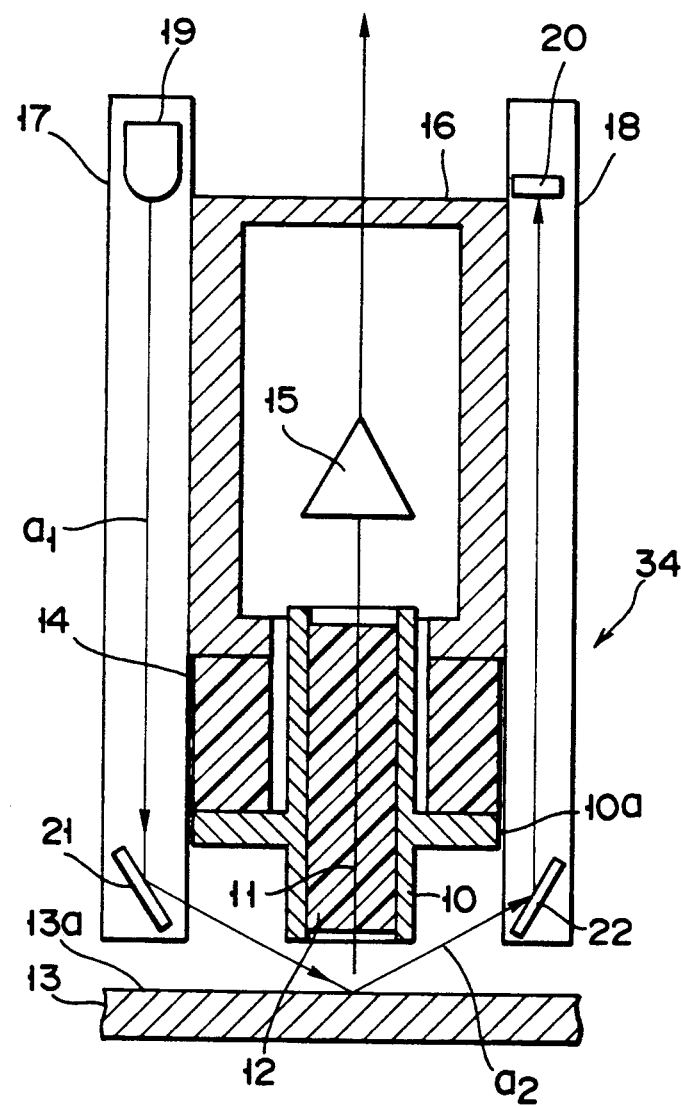
FIG. 4 is a sectional view showing a vibration type probe structure according to another embodiment of the present invention.

FIG. 4 shows a vibration type probe structure according to another embodiment of the present invention. As shown in FIG. 4, a needle-like probe electrode 11 is inserted in a cylindrical housing 10 having a hinge portion 10a formed around its outer surface such that the distal end of the probe electrode 11 protrudes from the housing 10. The probe electrode 11 is fixed by an insulating material 12 such as Teflon filled in the housing 10. The distal end of the probe electrode 11 is located near and opposite a sample 13. A cylindrical piezoelectric element 14 is arranged around the outer surface of the housing 10. The lower portion of the piezoelectric element 14 is fixed to the hinge portion 10a of the housing 10. The upper portion of the piezoelectric element 14 is fixed to the lower portion of a case 16 in which an amplifier 15 connected to the probe electrode 11 is housed. Mirror cases 17 and 18 are arranged outside the piezoelectric element 14 and the case 16 so as to be symmetrical about the probe electrode 11. A light source 19 such as a laser diode (LD) for emitting a light beam and a PSD (semiconductor position detecting element) 20 as a position sensor for detecting the position of a light beam are respectively arranged in the upper portions of the mirror cases 17 and 18. Mirrors 21 and 22 are respectively arranged in the lower portions of the mirror cases 17 and 18. The mirror 21 is positioned to cause a laser beam a1 emitted from the light source 19 to be incident on a measurement surface 13a of the sample 13 located right under the distal end of the probe electrode 11. The mirror 22 is positioned to guide a laser beam a2 reflected by the measurement surface 13a to the PSD 20. The mirrors 21 and 22 are located near the sample 13 so as to increase the incident angle of the laser beam which is incident on the measurement surface 13a located right under the probe electrode 11 and to increase the reflection angle of the laser beam. Lens systems (not shown) for transmitting laser beams are respectively arranged between the light source 19 and the mirror 21 in the mirror case 17 and between the PSD 20 and the mirror 21 in the mirror case 18. An oscillator and a piezoelectric driver are connected to the piezoelectric element 14.

In the vibration type probe structure shown in FIG. 4, the oscillator is oscillated to generate an oscillation signal, and the oscillation signal is amplified by the piezoelectric driver so as to vertically vibrate the piezoelectric element 14. With this operation, the housing 10 having the hinge portion 10a to which the lower portion of the piezoelectric element 14 is fixed, and the probe electrode 11 fixed in the housing 10 with the insulating material 12 are vertically vibrated at the oscillation frequency of the oscillator. When the probe electrode 11 is vertically vibrated at a predetermined period, since the distance between the probe electrode 11 and the measurement surface 13a of the sample 13 located thereunder is periodically changed, some of lines of electric force generated from the measurement surface 13a reach the probe electrode 11 in accordance with the period. A signal detected by the probe electrode 11 is generated as an AC signal which has the oscillation period of the piezoelectric element 14 and is proportional to the surface potential of the measurement surface 13a. The AC signal is amplified by the amplifier 15, and is output as a measurement signal corresponding to the surface potential of the measurement surface 13a through a detector system constituted by a synchronous detection circuit, an integrator, and the like.

In this measurement process, the laser beam a1 emitted from the light source 19 is reflected by the mirror 21 so as to be incident on the measurement surface 13a of the sample 13 located right under the distal end of the probe electrode 11. The reflected laser beam a2 is then guided to the PSD 20 through the mirror 22. If the sample 13 is displaced vertically, i.e., in the height direction, the reflected laser beam a2 is deflected in accordance with the displacement amount, and the incident position of the beam on the PSD 20 is horizontally moved. By extracting an electrical signal proportional to this movement amount from the PSD 20, the vertical displacement amount of the measurement surface 13a with respect to a reference surface, i.e., the bottom surfaces of the mirror cases 17 and 18 can be measured. Therefore, even if the sample 13 is vertically displaced, the distance between the distal end of the probe electrode 11 and the sample 13 can be accurately measured. Consequently, even if the sample 13 has poor surface precision or the sample 13 is rotated or moved, an accurate measurement value can be obtained by correcting a detection voltage (AC signal) detected by the probe electrode 11 in accordance with the displacement amount of the sample Since the piezoelectric element 14 for vibrating the probe electrode 11 is formed to have a cylindrical shape and is fixed to the hinge portion 10a of the housing 10 in which the probe electrode 11 is fixed with the insulating material 12, a space is formed above the probe electrode 11. With this arrangement, the amplifier 15 for amplifying a detection voltage (AC signal) detected by the probe electrode 11 can be located near and connected to the upper portion of the probe electrode 11. Therefore, the influences of external noise and the like on a detection signal detected by the probe electrode 11 can be reduced, and a high-precision measurement value can be obtained.

In addition, since the distal end of the probe electrode 11 can be located near the sample 13, excellent detection sensitivity can be realized, and the measurement resolution can be increased, thus allowing high-precision measurement of a surface potential within a small area.

Figure 5:
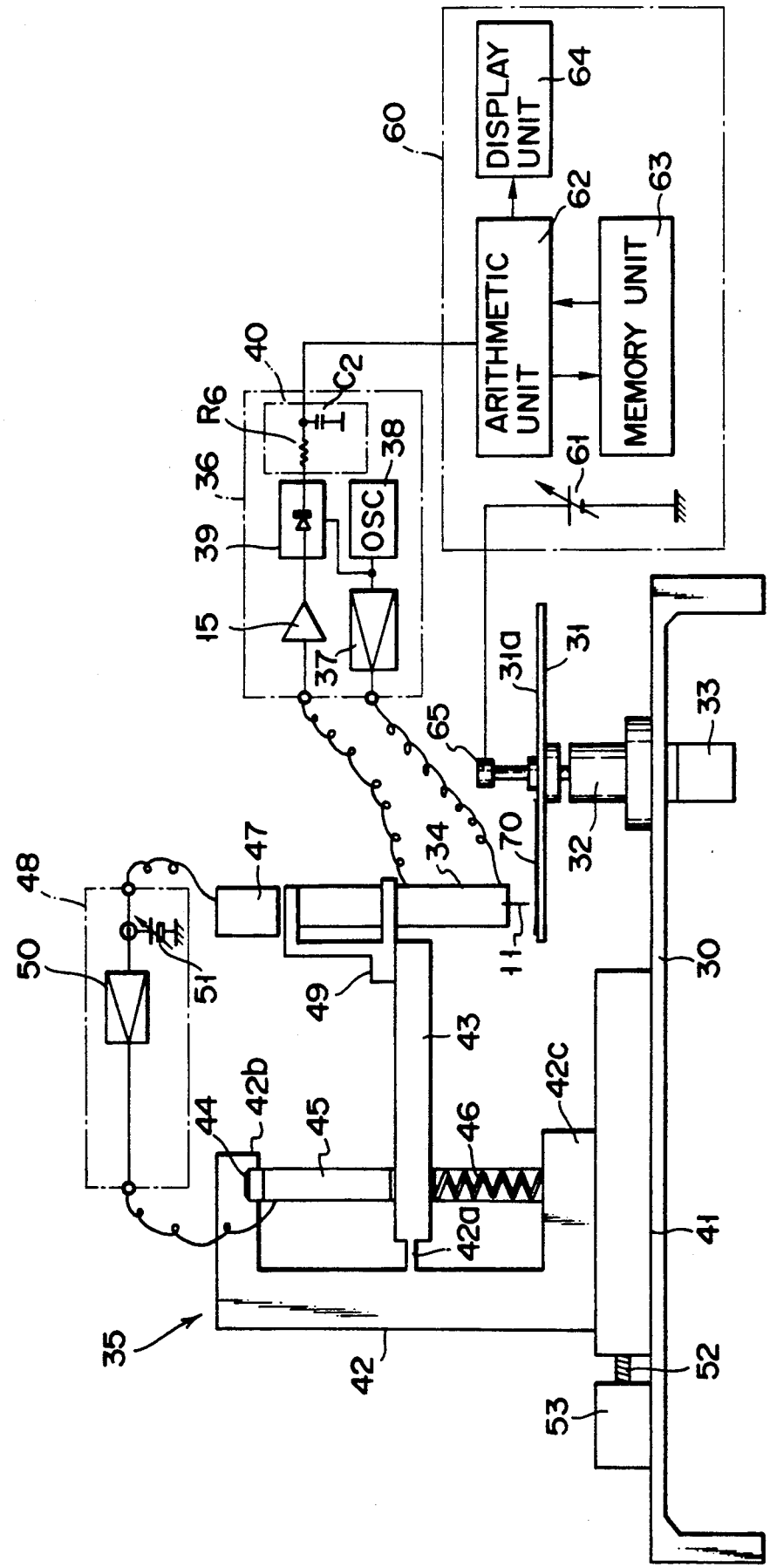
FIG. 5 is a block diagram showing a system for measuring the surface potential of a sample, which incorporates the vibration type probe structure in FIG. 4.

FIG. 5 shows a system, having the vibration type probe structure shown in FIG. 4, for measuring the potential distribution of a surface of a sample. As shown in FIG. 5, a spindle 32, a driving motor 33, and a gap control unit 35 are arranged on an antivibration base 30. The spindle 32 serves to rotate a disk-like sample 31. A vibration type probe structure 34 for measuring the surface potential of a measurement surface 31a of the sample 31 is mounted on the gap control unit 35. In addition, this system includes a surface potential detector 36 for receiving a signal detected by the vibration type probe 34 and outputting a measurement value corresponding to the surface potential of the measurement surface 31a, and a measurement value correcting unit 60 for correcting the measurement value.

Figure 6:
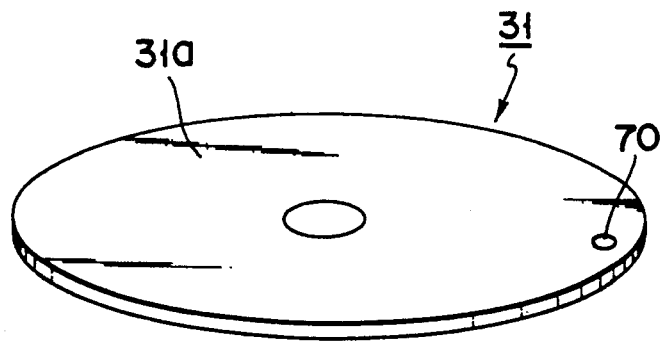
FIG. 6 is a perspective view showing a sample whose surface potential is measured by the surface potential measuring system in FIG. 5.

As shown in FIG. 6, a correcting electrode 70 is formed at a peripheral portion on the measurement surface 31a of the sample 31. The correcting electrode 70 is formed by depositing a chromium pattern having a thickness of several hundreds Å and a width of several mm (outermost periphery). A reference voltage is applied from a reference power source 61 to the correcting electrode 70 through a rotary connector 65. This correcting electrode 70 may be formed on a table for supporting a sample instead of forming it on the sample 31.

The detector 36 arranged above the vibration type probe structure 34 comprises a piezoelectric element driver 37, an oscillator 38, a synchronous detection circuit 39, an integrator 40 consisting of a resistor R6 and a capacitor C2, and the above-mentioned amplifier 15. A signal generated by the oscillator 38 is amplified by the piezoelectric element driver 37 so as to drive the piezoelectric element 14. As a result, the probe electrode 11 is vertically vibrated.

The gap control unit 35 comprises: a table 41 movably mounted on the antivibration base 30; a main body 42 fixed to the table 41; an arm 43 substantially parallel to the sample 31 and integrally coupled to the main body 42, through an elastic hinge portion 42a; a gap control coupling spring 46 for coupling a gap control piezoelectric element 45, which is coupled between a protruding portion 42b formed on the upper portion of the main body 42 and the arm 43 through a gap adjusting screw 44, between a protruding portion 42c formed on the lower portion of the main body 42 and the arm 43; a gap detector 47 connected between the vibration type probe 34 and the piezoelectric element 45; and a gap control circuit 48.

The vibration type probe structure 34 is attached to a support member 49 fixed to the distal end of the arm 43. The distal end of the probe electrode 11 is located near the measurement surface 31a of the sample 31 (with a gap of about several tens μm) so as to oppose the measurement surface 31a and to be movable along its radial direction. A gap between an unvibrated end of the structure 34 and the measurement surface 31a is controlled by the gap control unit. That is, the gap between the vibrating center of the distal end of the probe electrode 11 and the measurement surface 31a is controlled by the gap control unit 35.

The gap control circuit 48 comprises a differential amplifier 50 and a variable voltage power source 51 for generating a gap setting voltage, i.e., a reference voltage. The piezoelectric element 45 is arranged on the side of the elastic hinge portion 42a at a position where the arm 43 is divided at a ratio of, e.g., 1 to 10. In addition, a driving motor 53 is coupled to the table 41 through a feed screw bar 52. When the feed screw bar 52 is rotated by the driving motor 53, the table 41 is laterally moved. Upon this movement, the probe electrode 11 of the vibration type probe structure 34 attached to the distal end of the arm 43 is moved along the radial direction of the measurement surface 31a of the sample 31.

An operation of the system which has the above-described arrangement and serves to measure a surface potential distribution will be described below.

The sample 31 mounted on the spindle 32 is rotated by the driving motor 33 at a predetermined speed. The probe electrode 11 is moved from the outer periphery of the measurement surface 31a toward its center (may also be moved in the opposite direction) upon driving of the driving motor 53. In the above-described manner, the surface potential of the measurement surface 31a is measured. More specifically, an oscillation signal from the oscillator 38 is amplified by the piezoelectric element driver 37 so as to vertically vibrate the cylindrical piezoelectric element 14. Since the piezoelectric element 14 is fixed to the hinge portion 10a of the housing 10, the housing 10 is vibrated integrally with the piezoelectric element 14. Upon this vibration, the probe electrode 11 fixed in the housing 10 with the insulating material 12 is also vertically vibrated at the oscillation frequency of the oscillator 38. When the probe electrode 11 is vertically vibrated at a predetermined period, since the distance (gap) between the probe electrode 11 and the measurement surface 31a of the sample 31 located thereunder is periodically changed, some of lines of electric force extending from the measurement surface 31a reach the probe electrode 11 in accordance with the period. Therefore, a signal detected by the probe electrode 11 is obtained as an AC signal which has the same vibration period as that of the piezoelectric element 14 and is proportional to the surface potential of the measurement surface 31a. This AC signal is amplified by the amplifier 17. The amplified signal is then subjected to synchronous detection at the same period as the oscillation period of the oscillator 38 and is averaged by the integrator 40. As a result, the signal is output as a measurement value corresponding to the surface potential of the measurement surface 31a.

In this manner, the surface potential of the measurement surface 31a of the sample 31 is measured. Although the measurement value includes an error due to drift such as temperature drift, the error is corrected by the measurement value correcting unit 60. More specifically, a reference voltage is applied to the correcting electrode 70, which is formed on a portion of the measurement surface 31a or of the table for supporting the sample in advance, through the rotary connector 65. The surface potential of the correcting electrode 70 is then measured by the measuring system in the same manner as described above. The detection voltage corresponding to the surface potential of the correcting electrode 70, i.e., a detection signal E1 is stored in a memory storage unit 63. Thereafter, the sample 31 is rotated, and the surface potential of the measurement surface 31a is measured as described above, and is stored in the memory unit 63. The sample 31 is rotated to measure the surface potential of the correcting electrode 70 again. A detection voltage E2 measured at this time is stored in the storage unit 63.

The detection signals E1 and E2 stored in the memory unit 63 are input to an arithmetic unit 62 so as to calculate the difference between the detection voltages E1 and E2 as a drift voltage E3 (= the detection voltage E1 − the detection voltage E2). The drift voltage E3 is subtracted from the measurement data of the surface potential of the measurement surface 31a stored in the memory unit 63, and a measurement value upon drift correction is displayed on a display unit 64.

Similar to the above-described operation, the probe electrode 11 is moved from the outer periphery of the measurement surface 31a toward its center (or in the opposite direction), and the surface potential of the correcting electrode 70 is measured at a position, which is assumed after the sample 31 is rotated once or a predetermined number of times as in the above-described manner, before and after measurement of the surface potential of the measurement surface 31a, and the difference between the measured surface potentials, i.e., a drift voltage is obtained. The measurement value, i.e., the surface potential of the measurement surface 31a is then corrected by subtracting the drift voltage from the measurement data based on the surface potential of the measurement surface 31a.

According to another embodiment, a reference voltage (E11, E12, E13 ... E1N) applied from the reference power source 61 to the correcting electrode 70 through the rotary connector 65 is linearly changed every time the probe electrode 11 is located right under the correcting electrode 70 formed on the measurement surface 31a while the probe electrode 11 is moved from the outer periphery of the measurement surface 31a of the rotating sample 31 toward its center (or in the opposite direction), and the applied voltage (E11, E12, E13 ... E1N) at each time is stored. Detection voltages (E21, E22, E23 ... E2N) which are output from the surface potential detector 36 of a surface potential measuring system at the respective timings are stored in the memory unit 63. The applied voltages (E11, E12, E13 ... E1N) and the detection voltages (E21, E22, E23 ... E2N) stored in the storage unit 63 are input to the arithmetic unit 62. The applied voltages (E11, E12, E13 ... E1N) are then respectively compared with the detection voltages (E21, E22, E23 ... E2N) so as to calculate linearity of the gain of the surface potential measuring system. The surface potential measurement data of the measurement surface 31a is corrected on the basis of this calculation result and is displayed on the display unit 64.

In the above-described embodiments, the measurement value of the surface potential of the measurement surface 31a which is subjected to drift correction is displayed on the display unit 64. However, the measurement value may be stored in the storage unit 63 so as to be read out as needed.

Figures 7A, 7B:
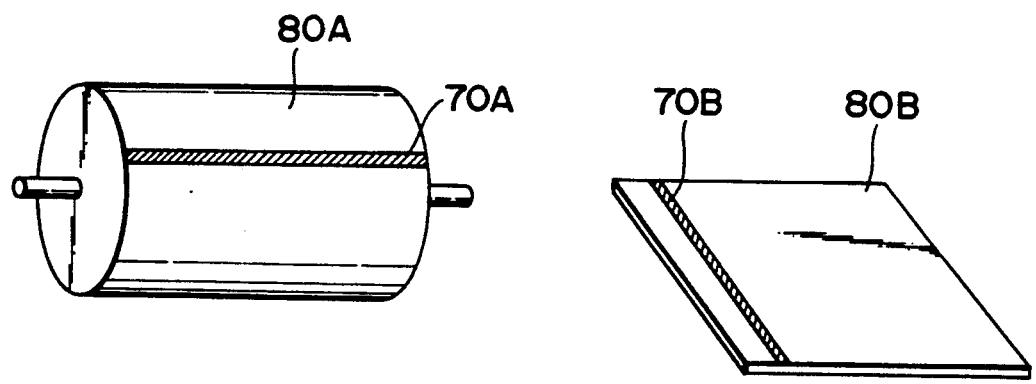
FIGS. 7A, 7B, and 7C are perspective views respectively showing other samples whose surface potentials are measured by the surface potential system in FIG. 5.
Figure 7C:
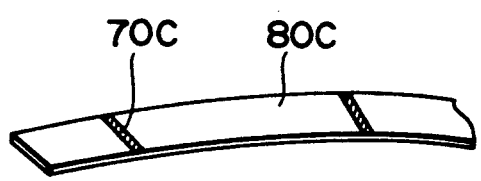
Figure 8:
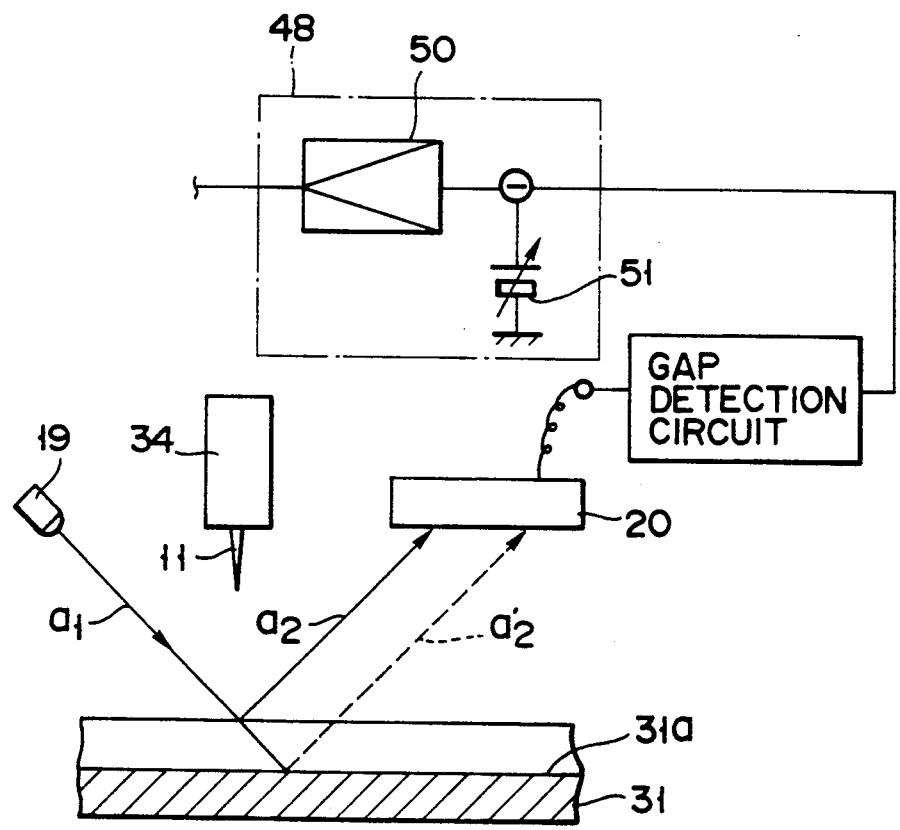
FIG. 8 is a view for explaining a principle of measuring a gap length between the probe electrode and a surface of the sample in FIG. 4.

Furthermore, in the above-described embodiments, the correcting electrode 70 is formed on a portion of the disk-like sample 31. However, measurement values can be corrected in the same manner as described above by forming correcting electrodes 70A, 70B, and 70C on portions of drum-like, card-like, and tape-like samples 80A, 80B, and 80C, respectively, as shown in FIG. 7A, 7B, and 7C. As evident from the above, it is not limited that the sample may be formed into not only a disk shape but also another shapes.

Assume that the gap length between the distal end of the probe electrode 11 and the measurement surface 31a varies during measurement of the surface potential of the measurement surface 31a due to poor surface precision of the measurement surface 31a or poor rotation precision of the sample 31. In such a case, the gap between the vibration center of the distal end of the probe electrode 11 and the measurement surface 31a is controlled to be constant by adjusting the variation amount. Such a gap control operation will be described below.

A laser beam a1 is emitted from the light source 19 and is incident through the lens system (not shown) and the mirror 21 on the measurement surface 31a of the sample 31 located right under the distal end of the probe electrode 11. A reflected laser beam a2 is guided to the PSD 20 through the mirror 22. At this time, if the surface precision of the measurement surface 31a or the rotation precision of the sample 31 is poor, the sample 31 is displaced vertically, i.e., in the height direction. If the sample 31 is displaced vertically, i.e., in the height direction, a reflected laser beam a2' of the laser beam a1 incident on the measurement surface 31a is incident on the PSD 20 while it is horizontally shifted by an amount as proportional to the displacement amount of the sample 31. An output signal from the PSD 20 is input to the gap detector 47 and is converted into a voltage having a constant level corresponding to the displacement amount of the sample 31. An output signal from the gap detector 47 is compared with a gap setting voltage, i.e., a reference voltage which is set in the variable voltage power source 51 of the gap control circuit 48. The difference between the voltages, i.e., a differential voltage is then output to the differential amplifier 50. The amplifier 50 amplifies the input differential voltage and applies it to the ga control piezoelectric element 45. The piezoelectric element 45 expands/contracts in proportion to the applied differential voltage. The arm 43 then vertically pivots on the elastic hinge portion 42a due to the expansion/contraction of the piezoelectric element 45 and the biasing force of the spring 46. As a result, the gap between the vibrating center of the probe electrode 11 of the vibration type probe 34 attached to the distal end of the arm 43 and the measurement surface 31a is controlled to be constant. At this time, since the distance between the elastic hinge portion 42a and the piezoelectric element 45 and the distance between the piezoelectric element 45 and the distal end of the arm 43 are set to be 1:10, the displacement amount of the probe electrode 11 of the probe 34 attached to the distal end of the arm 43 is increased to 10 times the expansion/contraction amount of the piezoelectric element 45. Hence, the displacement amount of the probe electrode 11 becomes large. For example, when the expansion/contraction amount of the piezoelectric element is 20 $\mu$m, the displacement amount of the probe electrode 11 has a dynamic range of 200 $\mu$m.

The gap between the vibrating center of the probe electrode 11 and the measurement surface 31a can be controlled to be constant by driving the driving motor 53 to rotate the feed screw bar 52 and moving the table 41 toward the sample 31. With this control, the surface potential of the entire measurement surface 31a can be easily, accurately, and stably measured.

By shielding the surface potential measuring system shown in FIG. 4 from external electric waves, more accurate measurement can be performed.

In the above-described embodiment, the surface potential of the disk-like sample is measured. However, measurement of a surface potential can be performed in the same manner as described above with respect to a flat, i.e., a card-like, drum-like, tape-like sample or another shape sample.

Figure 9:
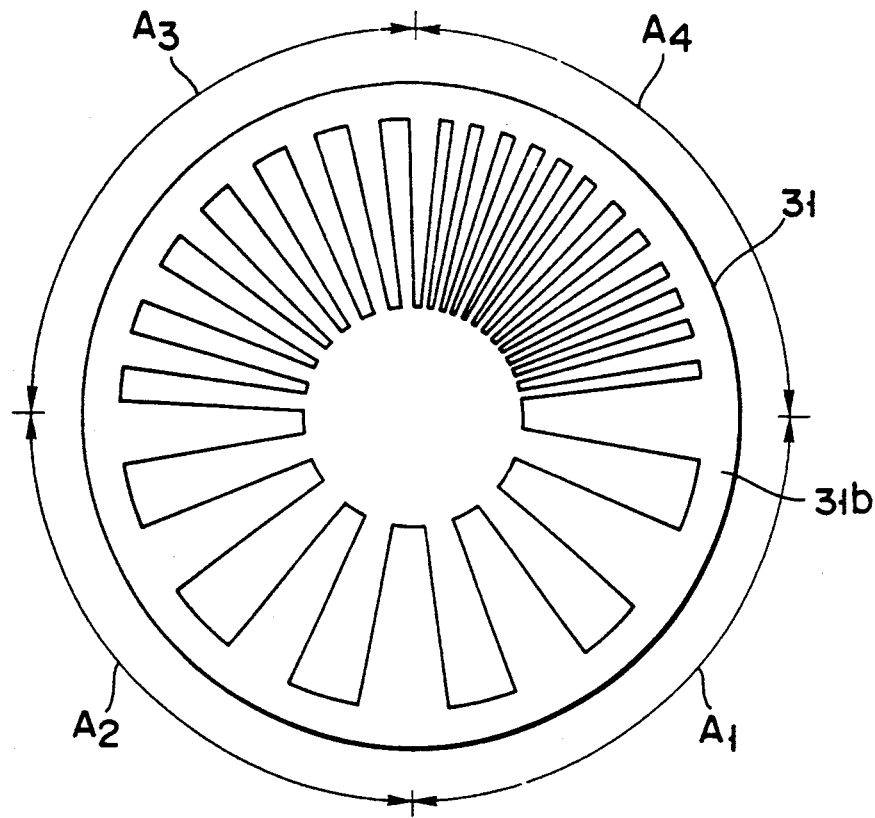
FIG. 9 is a plan view showing the sample on which a measurement experiment of a surface potential is performed by the system in FIG. 4.

FIGS. 9 to 12 show a sample on which measurement experiments are performed by mean of the surface potential distribution measuring system shown in FIG. 3, and measurement experiment results. As shown in FIG. 9, radial chromium patterns 31b are deposited on a measurement surface 31a of a disk-like sample 31. The intervals of the chromium patterns 31b vary from the outer periphery to the inner periphery. For example, the chromium patterns 31b are divided into four quadrants A1, A2, A3, and A4 at angular intervals of 90°. The quadrant A1 constitutes a 0.3 lines/mm (lp/mm) zone; the quadrant A2, a 2 lp/mm zone; the quadrant A3, a 4 lp/mm zone; and the quadrant A4, a 6 lp/mm zone. Note that all the values described above are values at the outermost periphery.

Figure 10:
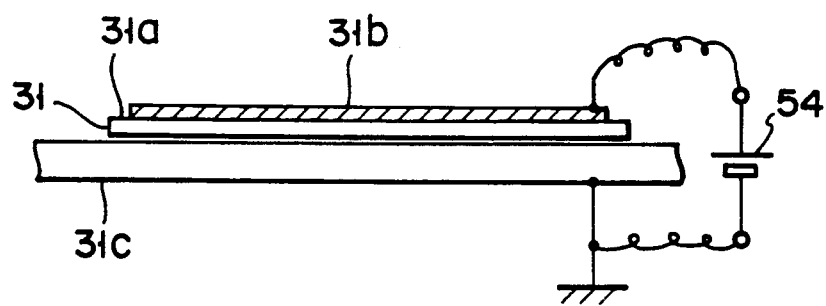
FIG. 10 is a sectional view of the sample in FIG. 9.

As shown in FIG. 10, the sample 31 is fixed on a disk base 31c, and a power source 54 is connected between the chromium patterns 31b and the disk base 31c. A predetermined voltage is applied to the chromium patterns 31b, and the sample 31 and the disk base 31c are rotated. The probe electrode is then located near the chromium patterns 31b. A surface potential on the chromium patterns 31b is measured in the same manner as in the above-described embodiments.

Figure 11:
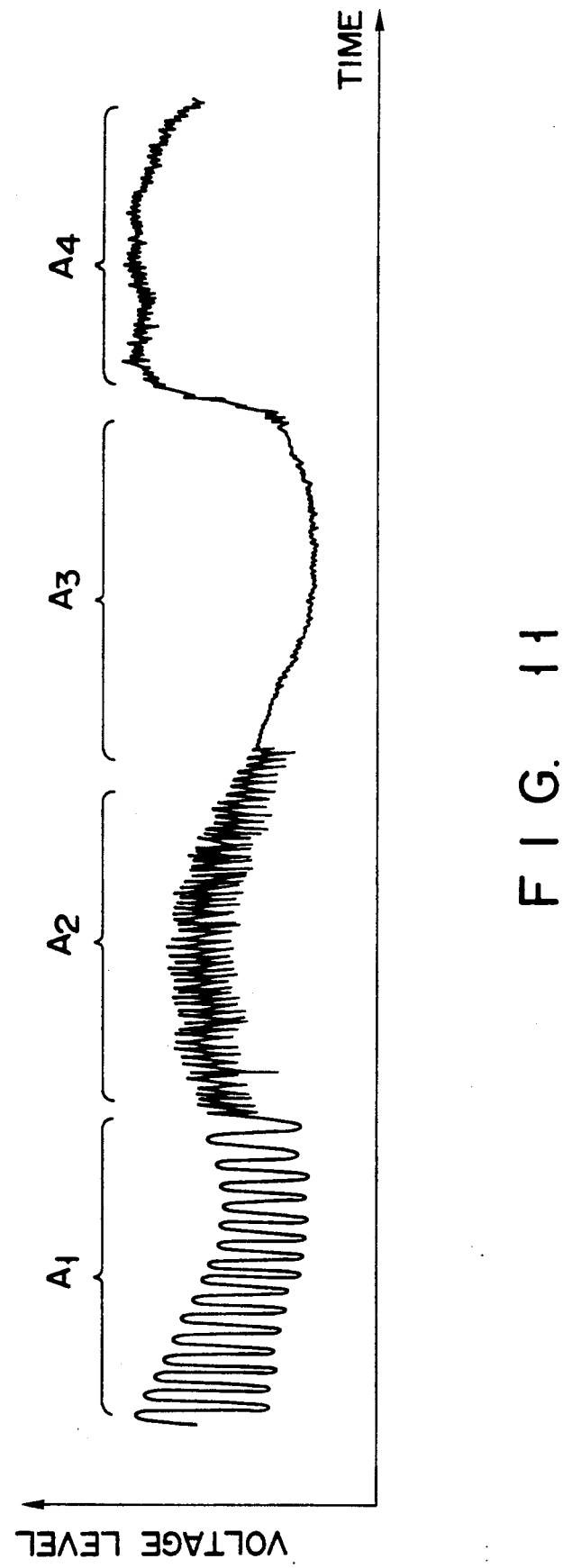
FIGS. 11 and 12 are graphs showing measurement results of measurement experiments.

FIG. 11 shows a experiment result obtained by measuring the surface potential of the sample by using the system shown in FIG. 5 without operating the gap control circuit 48 and performing gap control. In this measurement experiment, the probe electrode 11 is vibrated at a frequency of 7 kHz. Note that the abscissa and the ordinate in FIG. 11 respectively represent time and a measurement output, i.e., an output voltage. As shown in FIG. 11, in this system, the influences of variations in gap between the probe electrode and the sample are directly reflected in the output result, and the small chromium patterns in the quadrants A3 and A4 are not resolved. Hence, it is apparent that detection sensitivity in these quadrants is poor. However, relatively accurate measurement of surface potentials is performed in other quadrants A1 and A2. As is apparent from an experiment result to be described later, the surface potential of a sample can be measured with sufficient precision without gap control by increasing the vibration frequency of the probe 11.

Figure 12:
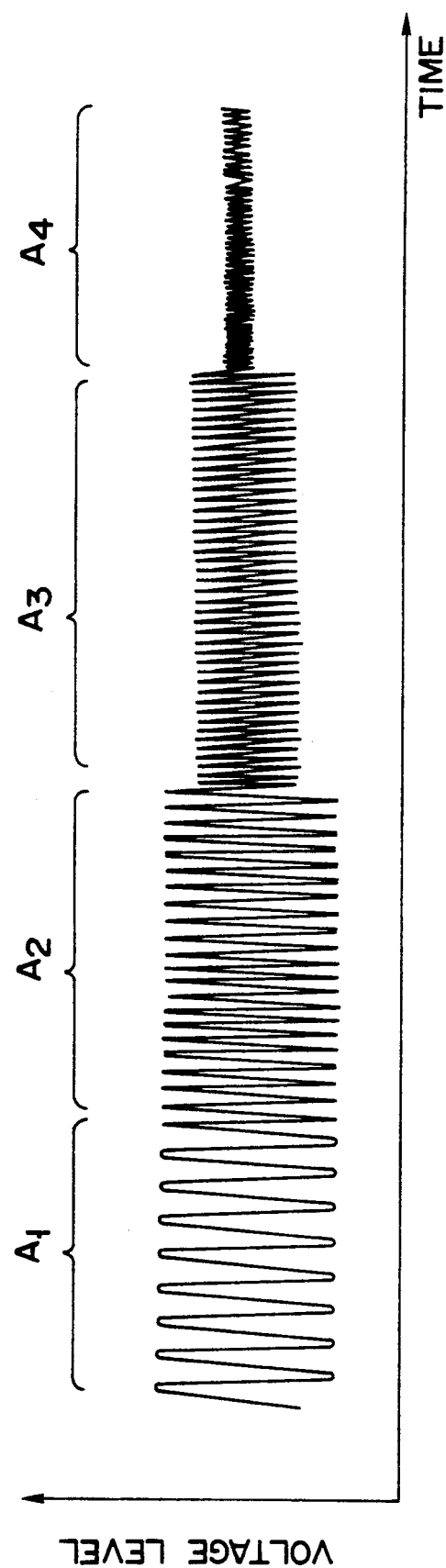

FIG. 12 shows an experiment result obtained by measuring the surface potential of a sample by using the system shown in FIG. 5. In this case, the gap control circuit 48 is operated to perform gap control. In this measurement experiment, the probe electrode 11 is vibrated at a frequency of 7 kHz. The sample 31 is rotated once and a voltage of 50 V is applied to the chromium patterns 31b. The gap between the probe electrode 11 and the chromium patterns 31b is held at 50±0.8 μm, and the surface potentials of the outer peripheral portions of the chromium patterns 31b are measured. Note that the abscissa and the ordinate in FIG. 12 respectively represent time and a measurement output, i.e., an output voltage. As shown in FIG. 12, according to the surface potential measuring system of the present invention, all the chromium patterns in the quadrants A1, A2, A3, and A4 are stably resolved.

Figure 13A:
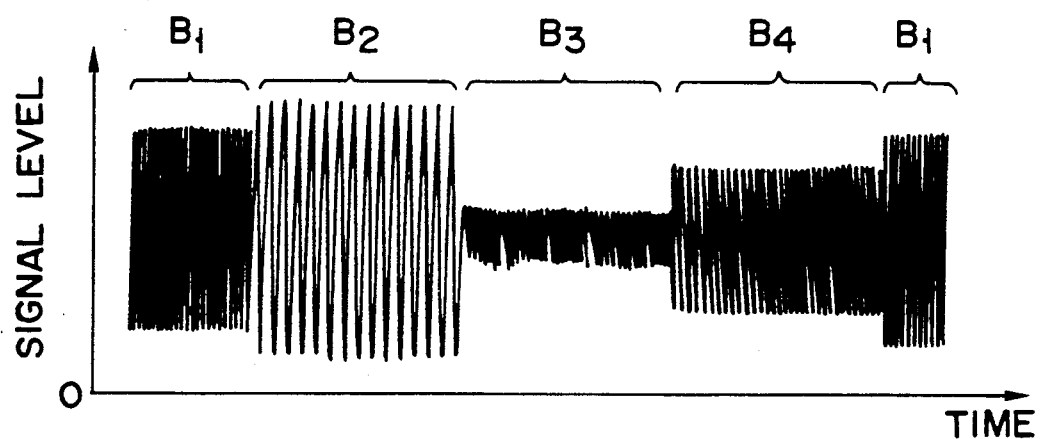
FIGS. 13A, 13B, and 13C graphs showing other experiment results obtained from measurement experiments performed by the system in FIG. 4.
Figure 13B:
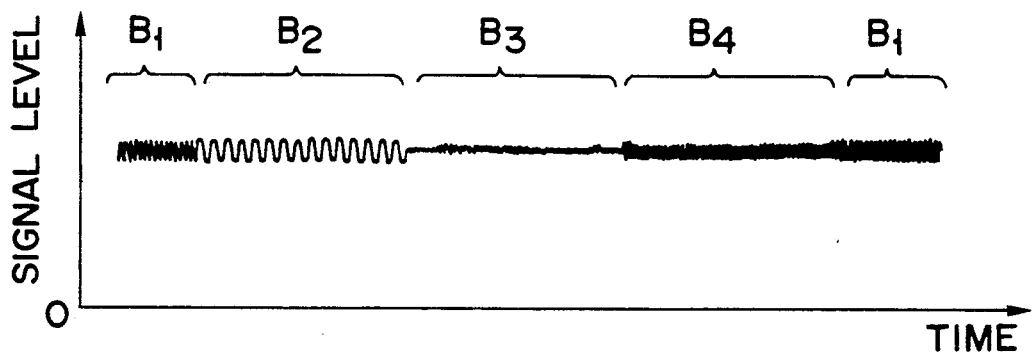
Figure 13C:
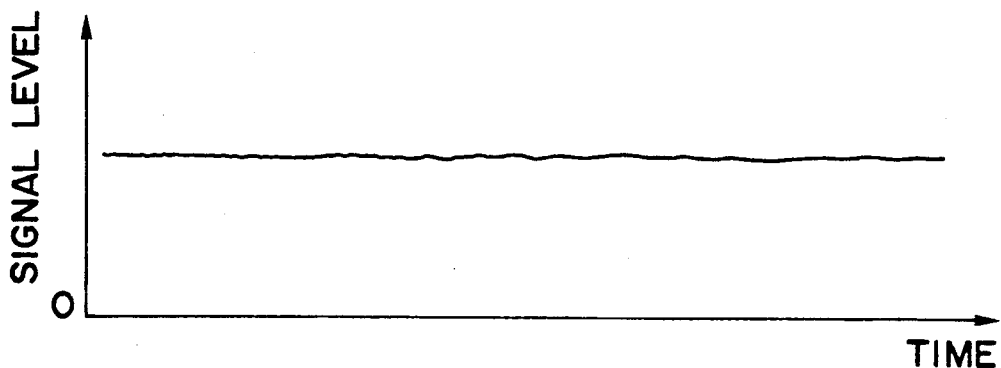

FIGS. 13A, 13B, and 13C respectively show experiment results obtained by measuring the surface potential of a sample by using the system shown in FIG. 5. In this case, the gap control circuit 48 is operated to perform gap control, and the probe electrode 11 is vibrated at 10 kHz, 1 kHz, and 0 kHz, respectively. In this experiment, similar to the disk-like sample shown in FIG. 9, radial chromium patterns 31b are deposited on a measurement surface 31a of a sample (not shown). The intervals of the chromium patterns 31b vary from the outer periphery to the inner periphery. For example, the chromium patterns 31b are divided into four quadrants B1, B2, B3, and B4 at angular intervals of 90°. The quadrant B1 constitutes a 2 lines/mm (lp/mm) zone; the quadrant B2, a 0.3 lp/mm zone; the quadrant B3, a 5 lp/mm zone; and the quadrant B4, a 3 lp/mm zone. Note that all the values described above are values at the outermost periphery. As is apparent from FIGS. 13A, 13B, and 13C, as the vibration frequency of the probe electrode 11 is increased, the potential of the sample can be measured with higher precision. In addition, it is found from experimental results that the surface potential of the sample can be satisfactorily measured even at a vibration frequency of 1 kHz and it is possible that the surface potential can be precisely measured at a vibration frequency of 10 kHz when the circuit arrangement is so improved as to have a high detection sensitivity.

It is confirmed, on the basis of the above-described experiment results and in consideration of various circuit systems, that the probe electrode 11 is preferably vibrated at 100 kHz or less, more preferably, between 50 kHz to 100 kHz.

In practice, the system for measuring the surface potential of a sample according to the present invention is applied to a radiation imaging apparatus for forming and observing a fluoroscopic image in a real size by using an image plate.

Figure 14:
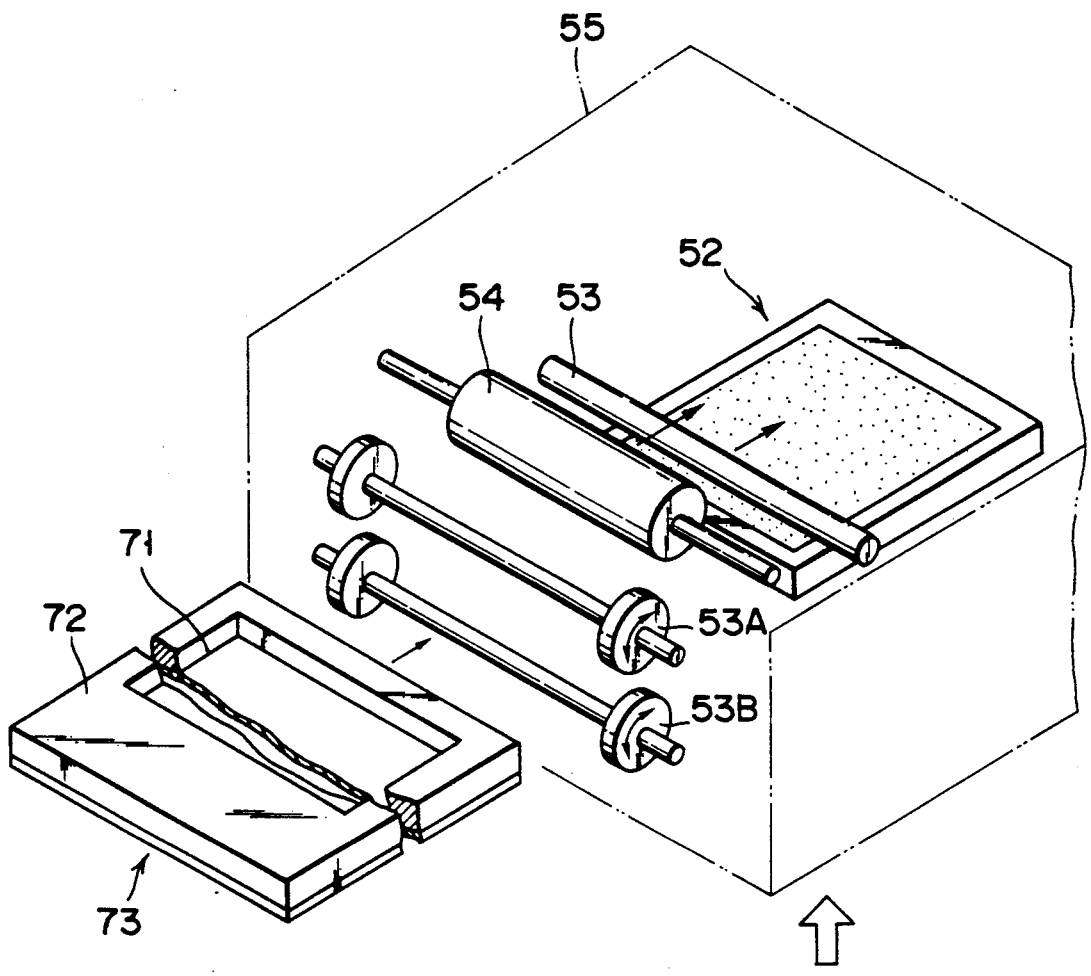
FIG. 14 is a perspective view showing a schematic arrangement of an X-ray imaging apparatus for transferring a latent image onto an image plate whose surface potential is measured by the measuring system of the present invention.

FIG. 14 shows an X-ray imaging apparatus. In this X-ray imaging apparatus, an image plate 52 for forming an X-ray image is housed in a casing 55. A window (not shown) is formed in the bottom of the casing 55. An X-ray transmission image is radiated onto the image plate 52 through this window.

Figure 15:
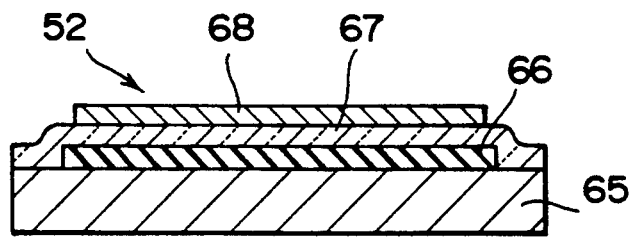
FIG. 15 is a sectional view showing an image plate in FIG. 14.

As shown in FIG. 15, the image plate 52 is formed by stacking a phosphor layer 66, an ITO layer 67, and a photosensitive layer 68 on an aluminum substrate 65. The phosphor layer 66 is constituted by a layer containing gadolinium, iodine, cesium, and the like, e.g., a $Gd_2O_2SiTb$ layer having a thickness of about 200 μm. The photosensitive layer 68 is constituted by a layer consisting of an inorganic or organic photosensitive substance, e.g., an amorphous Si layer having a thickness of about 20 μm. The gadolinium phosphor layer emits light having a peak at a wavelength of 550 nm upon radiation of X-rays, and hence has a very high luminous efficacy. The amorphous Si photosensitive layer has high sensitivity in a visible region, and has a quantum efficiency of nearly 100% with respect to light near 550 nm.

A high-voltage charger 53 for uniformly charging the image plate 52 is arranged in the casing 55. Prior to an imaging operation, the charger 53 is scanned/driven on the image plate 52 along a guide (not shown) with a small gap of about 5 mm ensured with respect to the image plate 52. With this operation, the entire surface of the image plate 52 is charged at, e.g., about 500 V.

A dielectric recording sheet 73 on which a latent image formed on the image plate 52 is transferred and recorded is prepared separately from the casing 55. The dielectric recording sheet 73 is formed by bonding a dielectric sheet 71 to a frame 72. The dielectric recording sheet 73 is inserted into an insertion port formed in a side portion of the casing 55. The sheet 73 is then clamped between a pair of loading/unloading rollers 53A and 53B and is transferred onto the image plate 52. A transfer roller 54 is arranged in the casing 55. When the dielectric recording sheet 73 is transferred onto the image plate 52, the transfer roller 54 is scanned/driven along a guide (not shown) while the roller 54 urges the sheet 73 against the image plate 52.

An imaging operation will be described in detail with reference to FIGS. 16A to 16E which sequentially show an operation of main part of the imaging apparatus in FIG. 15.

Figure 16A:
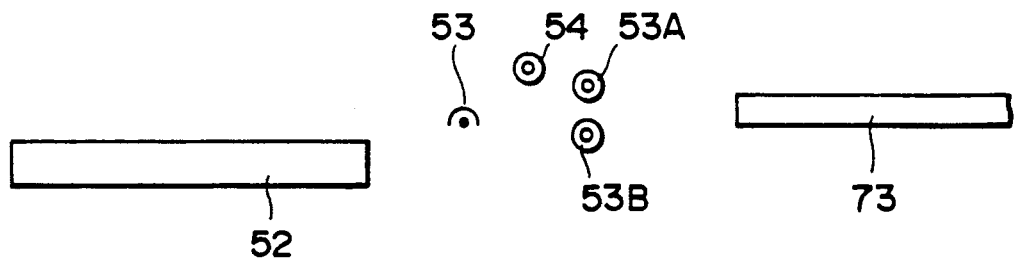
FIGS. 16A to 16E are views for explaining an imaging operation of the X-ray imaging apparatus shown in FIG. 14.
Figure 16B:
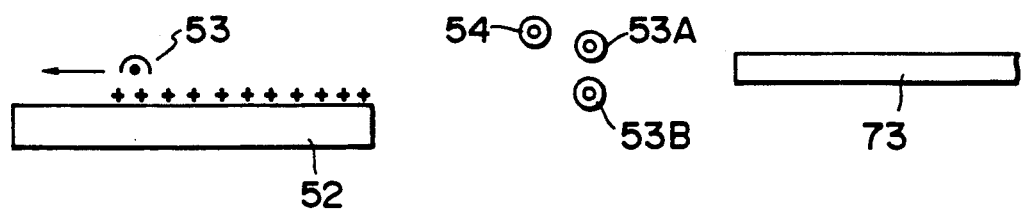
Figure 16C:
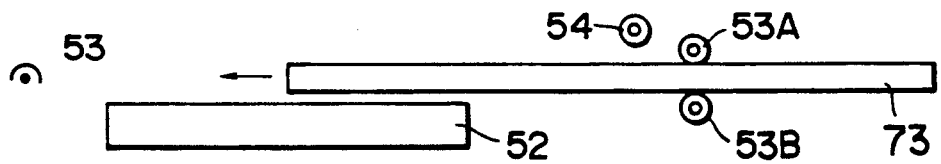

FIG. 16A shows a positional relationship between the respective portions before an imaging operation is started. An imaging operation is started when the charger 53 is scanned/driven on the image plate 52 upon depression of a start switch (not shown), as shown in FIG. 16B. Upon application of a high voltage of 4 to 7 kV from the charger 53, the image plate 52 is uniformly charged at about 500 V, as described above. This operation is equivalent to initialization of the image plate 52. As shown in FIG. 16C, the dielectric recording sheet 73 is then inserted. The sheet 73 is transferred onto the image plate 52, and is caused to oppose the image plate 52 with a gap of about 1 to 2 mm.

Subsequently, an X-ray transmission image is radiated from the substrate side of the image plate 52. If, for example, a human body is to be subjected to fluoroscopic imaging, X-ray radiation is performed at 70 keV and about 1 mR. Upon this X-ray radiation, a latent image is formed on the image plate 52. More specifically, the gadolinium phosphor layer emits visible light upon X-ray radiation, and the charges on the amorphous Si layer corresponding to the portions from which the light is emitted are discharged to the grounded substrate in accordance with the light emission amounts of the respective portions. As a result, a potential pattern of 500 to 50 V is formed in accordance with the transmission image.

Figure 16D:
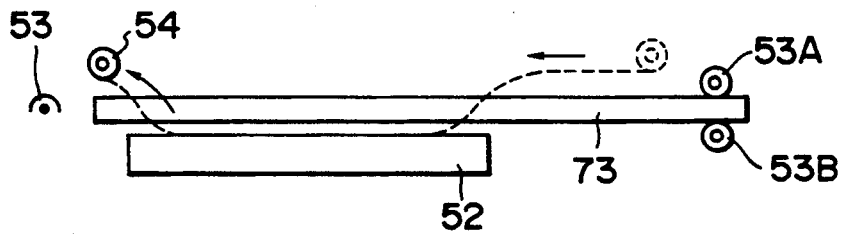
Figure 16E:
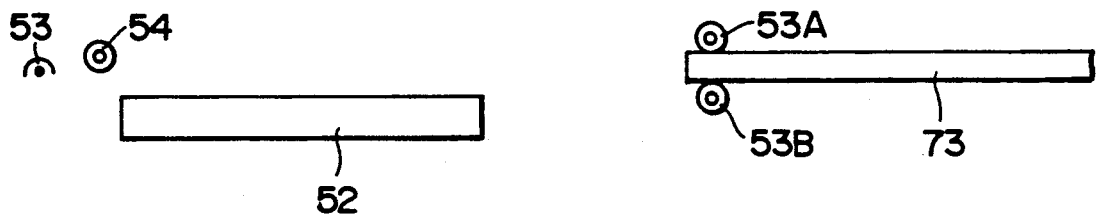

Subsequently, as shown in FIG. 16D, the transfer roller 54 is scanned/driven along the guide, and a dielectric sheet 71 of the dielectric recording sheet 73 is urged against the image plate 52. With this operation, the latent image on the image plate 52 is transferred onto the dielectric sheet 71. In this transfer process, a reference voltage is applied from an electrode (not shown) to the dielectric exhausted recording sheet 71. As described above, similar to a potential applied to the correcting electrode 70, this reference voltage is used for correction of a voltage from the surface potential measuring circuit 40 shown in FIG. 4. The dielectric recording sheet 73 on which the latent image is transferred and recorded is exhausted outside the casing by the rollers 53A and 53B, as shown in FIG. 16E. Thereafter, a new dielectric recording sheet is set, and the flow of processing returns to the step in FIG. 16A.

Figure 17:
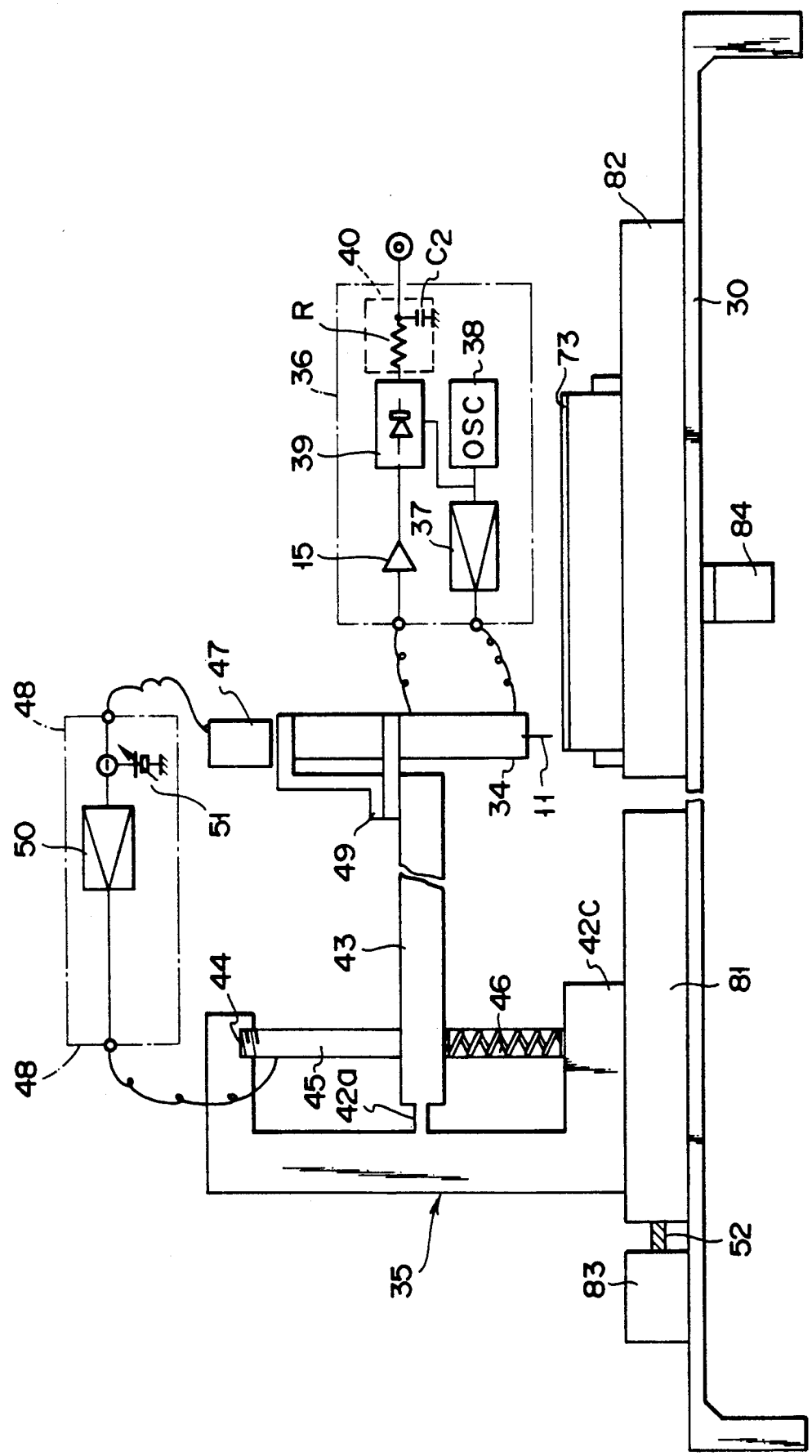
FIG. 17 is a block diagram showing a system for measuring an electrostatic potential for reading a recording sheet on which a latent image is transferred according to still another embodiment of the present invention.

The latent image formed on the recording sheet 73 in this manner is read by a surface potential measuring system shown in FIG. 17 having substantially the same arrangement as that of the system shown in FIG. 4.

The surface potential measuring system shown in FIG. 17 is different from the one shown in FIG. 4 in that X- and Y-axis tables 81 and 82 are arranged on a stage 30 so as to be driven by X- and Y-axis driving motors 83 and 84, respectively. The dielectric recording sheet 73 on which the latent image is formed is placed on the Y-axis table 82. From the sheet 73, the potential image is sequentially picked up by a probe electrode 11 which is slightly vibrated by a vibrating piezoelectric element, and is extracted, as an image signal, by a surface potential detector 40.

The vibrating piezoelectric element is attached to the distal end of an arm 43 of a gap control mechanism mounted on the X-axis table 81. The gap control mechanism includes a gap adjusting screw 44, a balancing spring 46, and a gap control mechanism driving piezoelectric element 45. This piezoelectric element is controlled by a gap control circuit 48 so that optimal control of the gap between the vibrating center of the probe electrode 11 attached to the distal end of the arm 43 and the recording sheet 73 is automatically performed.

For this gap control, a gap position detecting optical system and a gap detector 47 are coaxially arranged at a position where the probe electrode 11 is attached. With this arrangement, a light beam is radiated from the optical system onto the recording sheet 73. Upon detection of the light beam reflected by the sheet 73, the gap detector 47 detects a gap. The detected gap is then fed back to the piezoelectric element 45 through the gap control circuit 48.

In such a surface potential measuring system, while the probe electrode 11 is slightly vibrated, the gap between the vibrating center of the probe electrode 11 and the recording sheet 73 is accurately and automatically controlled, and the latent image on the recording sheet 73 is read by X-Y scanning.

As described above, according to the present invention, when a real-size X-ray transmission image is to be imaged, as a latent image, on a photosensitive layer and to be read, the latent image is first transferred and recorded on a dielectric recording image by urging the photosensitive layer against the recording sheet. With this operation, the image can be read without attenuation in the image potential, and hence a uniform reproduced image can be obtained.

In addition to the above-described X-Y scanning, the latent image on the dielectric recording sheet 73 can be read by the rotating disk type system shown in FIG. 4. In this case, a dielectric recording sheet having a rectangular frame must be transferred onto a disk.

Figure 18:
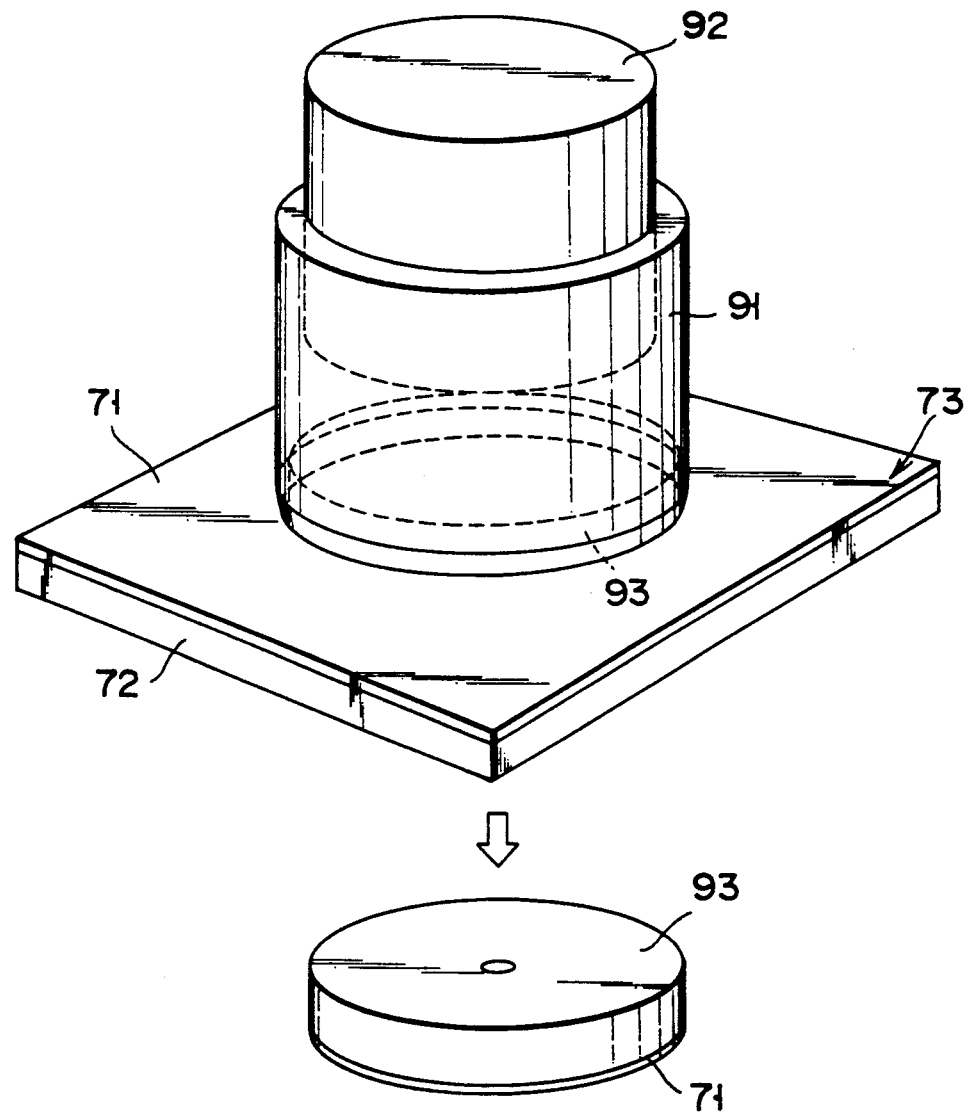
FIG. 18 is a perspective view showing a schematic arrangement of an apparatus constituting a rotating recording disk from which data can be read by the system in FIG. 4.

FIG. 18 shows a method for such an operation. In this method, the dielectric sheet 71 of the dielectric recording sheet 73 is cut by a cutting jig 91 and a press piston 92, and i simultaneously bonded to a disk 93. The cutting jig 91 has a cylindrical shape and a blade formed on its distal end. The press piston 92 is coaxially fitted in the cutting jig 91. The disk 93 has an outer diameter allowing it to be fitted in the jig 91. An adhesive agent is coated on the lower surface of the disk 93 in advance. While the disk 93 is fitted in the distal end of the cutting jig 91, the jig 91 is brought into contact with the dielectric sheet 71 on which a latent image is formed. By operating the press piston 92 and the cutting jig 91, the disk 93 is bonded to the sheet 71, and at the same time, the sheet 71 is cut off. With this process, a rotating disk on which the dielectric sheet 71 is bonded can be obtained. The image on the rotation disk is read by the system shown in FIG. 4.

The present invention is not limited to the above-described embodiment. In the embodiment, an X-ray transmission image is radiated from the substrate side of the image plate. However, since X-rays are transmitted except for the phosphor layer, an X-ray transmission image may be radiated from the upper surface side of the image plate.

According to the system shown in FIG. 17, when a real-size X-ray transmission image is to be formed by using an image plate, an excellent reproduced image can be obtained by preventing attenuation in the image potential of the photosensitive layer.

As has been described above, in the vibration type probe structure of the present invention, the distal end of the probe electrode is located near a measurement surface, and the surface potential of the measurement surface is measured by vibrating the probe electrode in a direction perpendicular to the measurement surface. With this arrangement, excellent detection sensitivity and high measurement resolution can be realized, thus enabling high-precision measurement in a small area.

In addition, according to the present invention, a reference voltage is applied to the correcting electrode formed on a portion of a measurement surface. A detection signal output from the surface potential measuring system at this time is input to the arithmetic means. With this operation, a measurement error of the surface potential of the measurement surface due to drift such as temperature drift can be corrected on the basis of the input detection signal. Therefore, a high-precision measurement value can be stably obtained.

Additional advantages and modifications will readily occur to those skilled in the art. Therefore, the invention in its broader aspects is not limited to the specific details, and representative devices, shown and described herein. Accordingly, various modifications may by without departing from the spirit or scope of the general inventive concept as defined by the appended claims and their equivalents.

What is claimed is:

1. A system for measuring a surface potential of a sample, comprising:
   probe means, having a distal end located near a measurement surface of the sample with a gap therebetween and having a vibrating center, for probing the surface potential;
   vibrating means for vibrating said probe means with respect to the vibrating center to change the gap between the distal end and the measurement surface;
   detecting means for detecting a change in potential of the distal end of said probe means and converting the change into a measurement signal corresponding to the surface potential of the sample; and
   means for controlling said vibrating means to maintain a constant distance between the vibrating center and the measurement surface.

2. A system according to claim 1, wherein said vibrating means vibrates the distal end of said probe means at a predetermined frequency not smaller than 1 kHz.

3. A system according to claim 1, wherein said vibrating means includes means for generating an oscillation signal having a predetermined frequency not smaller than 1 kHz and elongation and contraction means being elongated or contracted in response to the oscillation signal so as to vibrate said probe means.

4. A system according to claim 3, wherein said detecting means includes means for converting a potential of the distal end of said probe means into a potential signal, and detection means for detecting the potential signal with the oscillation signal and generating a measurement signal.

5. A system according to claim 4, wherein said detecting means further includes integrating means for integrating and averaging the measurement signal to generate an averaged measurement signal.

6. A system according to claim 1, further comprising means for displaying the measurement signal.

7. A system according to claim 1, wherein said vibrating means includes a piezoelectric element.

8. A system according to claim 1, wherein said probe means includes a probe electrode and means for supporting said probe electrode.

9. A system according to claim 8, wherein said supporting means includes a cylindrical housing in which said probe electrode is fixed, the distal end of said probe electrode being projected from said cylindrical housing.

10. A system according to claim 9, wherein said supporting means further includes an insulating member received in the cylindrical housing, said probe electrode being fixed by the insulating member in the cylindrical housing.

11. A system according to claim 9, further comprising:
means for shielding said probe means, said vibrating means and said detecting means from an electromagnetic wave.

12. A system according to claim 1, wherein said controlling means includes means for detecting a distance between the vibrating center and the measuring surface to generate a gap signal.

13. A system according to claim 12, wherein said controlling means includes means for moving said probe means which vibrates in response to the gap signal.

14. A system according to claim 1, further comprising means for moving the sample along the measurement surface.

15. A system according to claim 1, further comprising means for rotating the sample.

16. A system according to claim 1, further comprising reference means having a reference potential to be detected by said probe means.

17. A system according to claim 16, further comprising correcting means for correcting a measurement signal corresponding to the surface potential of the sample by using a measurement signal corresponding to the reference potential of said reference means which is converted by said detecting means.

18. A system according to claim 17, wherein said correcting means includes means for generating a correction signal by processing the measurement signal corresponding to the reference potential, and means for storing the correction signal.

19. A system according to claim 1, further comprising said probe means including a needle-like electrode having the distal end.

20. A system for measuring a surface potential of a sample, comprising:
probe means, having a distal end located near a measurement surface of the sample with a gap, for probing the surface potential;
vibrating means for vibrating said probe means to change the gap between the distal end and the measurement surface; and
detecting means for detecting a change in potential of the distal end of said probe means and converting the change into a measurement signal corresponding to the surface potential of the sample;
wherein said controlling means includes means for detecting a change of a gap between the surface of the sample and a given reference surface and generating a gap signal; and
wherein said means for generating the gap signal includes means for generating a light beam and directing the light beam to the measurement surface, and means for detecting the light beam reflected by the measurement surface, and detecting a displacement of the reflected beam which is dependent on a change of the sample with respect to the reference surface, thereby generating the gap signal.

21. A system for measuring a surface potential of a sample having a surface region, comprising:
probe means, having a distal end located near a measurement surface of the sample with a gap and having a vibrating center, for probing the surface potential of the measurement surface;
vibrating means for vibrating said probe means with respect to the vibrating center to change the gap between the distal end and the measurement surface;
holding means for holding said problem means so as to allow said probe means to be vibrated;
means for controlling the holding means to maintain a constant distance between the vibrating center and the measurement surface; and
detecting means for detecting a change in potential of the vibrated distal end of said probe means and converting the change into a measurement signal corresponding to the surface potential of the sample.

22. A system according to claim 21, wherein said vibrating means vibrates the distal end of said probe means at a predetermined frequency not smaller than 1 kHz.

23. A system according to claim 21, wherein said vibrating means includes means for generating an oscillation signal having a predetermined frequency not smaller than 1 kHz and elongation and contraction means being elongated or contracted in response to the oscillation signal so as to vibrate said probe means.

24. A system according to claim 23, wherein said detecting means includes mans for converting a potential of the distal end of said probe means into a potential signal, and detection means for detecting the potential signal with the oscillation signal and generating a measurement signal.

25. A system according to claim 24, wherein said detecting means further includes integrating means for integrating and averaging the measurement signal to generate an averaged measurement signal.

26. A system according to claim 21, further comprising means for displaying the measurement signal.

27. A system according to claim 21, wherein said vibrating means includes a piezoelectric element arranged between said holding means and said probe electrode.

28. A system according to claim 21, wherein said holding means includes a cylindrical housing in which said probe means is fixed, the distal end of said probe means being projected from said cylindrical housing.

29. A system according to claim 28, wherein said holding means further includes an insulating member received in the cylindrical housing, said probe means being fixed by the insulating member in the cylindrical housing.

30. A system according to claim 21, wherein said maintaining means includes means for detecting a change in height of the measurement surface with respect to a given reference surface and generating a height signal.

31. A system according to claim 30, wherein said maintaining means includes means for moving said holding means in response to the height signal.

32. A system for measuring a surface potential of a sample having a surface region, comprising:
 probe means, having a distal end located near a measurement surface with a gap therebetween, for probing the surface potential of the measurement surface;
 vibrating means for vibrating said probe means to change the gap between the distal end of said probe means and the measurement surface;
 holding means for holding said probe means which is vibrated by said vibrating means, so as to allow said probe means to be vibrated;
 means for maintaining a substantially constant gap between said holding means and a region detected by said probe means; and
 detecting means for detecting a change in potential of the vibrated distal end of said probe means and converting the change into a measurement signal corresponding to the surface potential;
 wherein said maintaining means includes means for detecting a change in height of the measurement surface with respect to a given reference surface and generating a height signal; and
 wherein said means for generating the height signal includes means for generating a light beam and directing the light beam to the measurement surface, and means for detecting the light beam reflected by the measurement surface, detecting a displacement of the reflected light beam which is dependent on a change in height of the measurement surface with respect to the reference surface, and generating a height signal.

33. A system according to claim 21, further comprising means for moving the sample along the measurement surface.

34. A system according to claim 21, further comprising means for rotating the sample.

35. A system according to claim 21, further comprising reference means having a reference potential to be detected by said probe means.

36. A system according to claim 35, further comprising correcting means for correcting a measurement signal corresponding to a surface potential of the sample by using a measurement signal corresponding to the reference potential of said reference means which is converted by said detecting means.

37. A system according to claim 36, wherein said correcting means includes means for generating a correcting signal by processing the measurement signal corresponding to the reference potential, and means for storing the correcting signal.

38. A system according to claim 21, further comprising:
 means for shielding said probe means, vibrating means and detecting means from an electro-magnetic wave.

39. A system according to claim 21, further comprising said probe means including a needle-like electrode having the distal end.

40. A system for measuring a surface potential of a sample, comprising:
 a needle electrode which has a distal end located near a measurement surface of the sample with a gap therebetween, for probing the surface potential;
 vibrating means for vibrating said needle electrode to change the gap between the distal end and the measurement surface;
 detecting means for detecting a change in potential of the distal end of said probe means and converting the change into a measurement signal corresponding to the surface potential of the sample; and
 means for controlling said vibrating means to maintain a constant distance between the vibrating center and the measuring surface;
 wherein said needle electrode has a vibrating center and said vibrating means vibrates said needle electrode with respect to the vibrating center.

41. A system for measuring a surface potential of a sample comprising:
 a needle electrode which has a distal end located near a measurement surface of the sample with a gap therebetween, for probing the surface potential;
 vibrating means for vibrating said needle electrode to change the gap between the distal end and the measurement surface;
 detecting means for detecting a change in potential of the distal end of said probe means and converting the change into a measurement signal corresponding to the surface potential of the sample; and
 controlling means for controlling a gap length between the distal end of said electrode and the measurement surface within a predetermined range.

42. A system according to claim 41, wherein said needle electrode is vibrated at a vibration frequency not smaller than 1 kHz.

43. A system according to claim 41, wherein said vibrating means includes means for generating an oscillation signal having a predetermined frequency not smaller than 1 kHz and elongation and contraction means being elongated or contracted in response to the oscillation signal so as to vibrate said probe means.

44. A system according to claim 41, wherein said detecting means includes means for converting a potential of the distal end of said probe means into a potential signal, and detection means for detecting the potential signal with the oscillation signal and generating a measurement signal.

45. A system according to claim 44, wherein said detecting means further includes integrating means for integrating and averaging the measurement signal to generate an averaged measurement signal.

46. A system according to claim 41, further comprising means for displaying the measurement signal.

47. A system according to claim 41, further comprising means for supporting said electrode.

48. A system according to claim 41, wherein said vibrating means includes a piezoelectric element.

49. A system according to claim 47, wherein said supporting means includes a cylindrical housing in which said electrode is fixed, the distal end of said electrode being projected from said cylindrical housing.

50. A system according to claim 49, wherein said supporting means further includes an insulating member received in the cylindrical housing, said electrode being fixed by the insulating member in the cylindrical housing.

51. A system according to claim 41, wherein said controlling means includes means for detecting a change of a gap between the surface of the sample and a given reference surface and generating a gap signal.

52. A system according to claim 51, wherein said controlling means includes means for moving said electrode which vibrates in response to the gap signal.

53. A system according to claim 51, wherein said means for generating the gap signal includes means for generating a light beam and directing the light beam to the measurement surface, and means for detecting the light beam reflected by the measurement surface, and detecting a displacement of the reflected beam which is dependent on a change of the sample with respect to the reference surface, thereby generating the gap signal.

54. A system according to claim 41, further comprising means for moving the sample along the measurement surface.

55. A system according to claim 41, further comprising means for rotating the sample.

56. A system according to claim 41, further comprising reference means having a reference potential to be detected by said electrode.

* * * * *

UNITED STATES PATENT AND TRADEMARK OFFICE
CERTIFICATE OF CORRECTION

PATENT NO. : 5,151,659
DATED : September 29, 1992
INVENTOR(S) : Kuniyoshi Tanaka et al.

It is certified that error appears in the above-identified patent and that said Letters Patent is hereby corrected as shown below:

On Title Page:

Item [30], the third Foreign Application Priority Data has been omitted, should be, --Feb. 14, 1990 [JP] Japan......2-31478--.

Signed and Sealed this

Fifth Day of October, 1993

Attest:

BRUCE LEHMAN

Attesting Officer     Commissioner of Patents and Trademarks